United States Patent [19]
Stouthamer et al.

[11] 3,981,923
[45] Sept. 21, 1976

[54] DEHYDROGENATION OF ALCOHOLS TO KETONES

[75] Inventors: Bernhard Stouthamer; Arien Kwantes, both of Amsterdam, Netherlands

[73] Assignee: Shell Oil Company, Houston, Tex.

[22] Filed: Sept. 16, 1974

[21] Appl. No.: 506,623

Related U.S. Application Data

[62] Division of Ser. No. 44,051, June 8, 1970, Pat. No. 3,875,239.

[30] Foreign Application Priority Data
June 11, 1969  Netherlands ................... 6908875

[52] U.S. Cl. ........................... 260/596; 252/472
[51] Int. Cl.² ................................. C07C 45/16
[58] Field of Search ............................ 260/596

[56] References Cited
UNITED STATES PATENTS

| | | |
|---|---|---|
| 2,885,442 | 5/1959 | McCullock ................... 260/596 |
| 3,053,898 | 9/1962 | Heuth ........................... 260/596 |
| 3,156,735 | 11/1964 | Armstrong ................... 260/596 |
| 3,499,938 | 3/1970 | Hwang .......................... 260/617 |

FOREIGN PATENTS OR APPLICATIONS

| | | | |
|---|---|---|---|
| 611,481 | 12/1960 | Canada ....................... 260/596 |
| 823,514 | 11/1959 | United Kingdom .......... 260/596 |

OTHER PUBLICATIONS
Davis et al., J. Catalyst 1969, 13(1) pp. 100–102.

*Primary Examiner*—James O. Thomas, Jr.
*Assistant Examiner*—James H. Reamer

[57] ABSTRACT

Controlling the average pore diameter of alumina-supported platinum or rhodium catalysts used for dehydrogenating lower secondary alcohol to ketones affects the product distribution. A large pore diameter gives high selectivities to the ketone corresponding in carbon number to the alcohol feed, whereas a small pore diameter permits coproduction of this lower ketone and economically attractive amounts of higher ketone condensation products.

3 Claims, 1 Drawing Figure

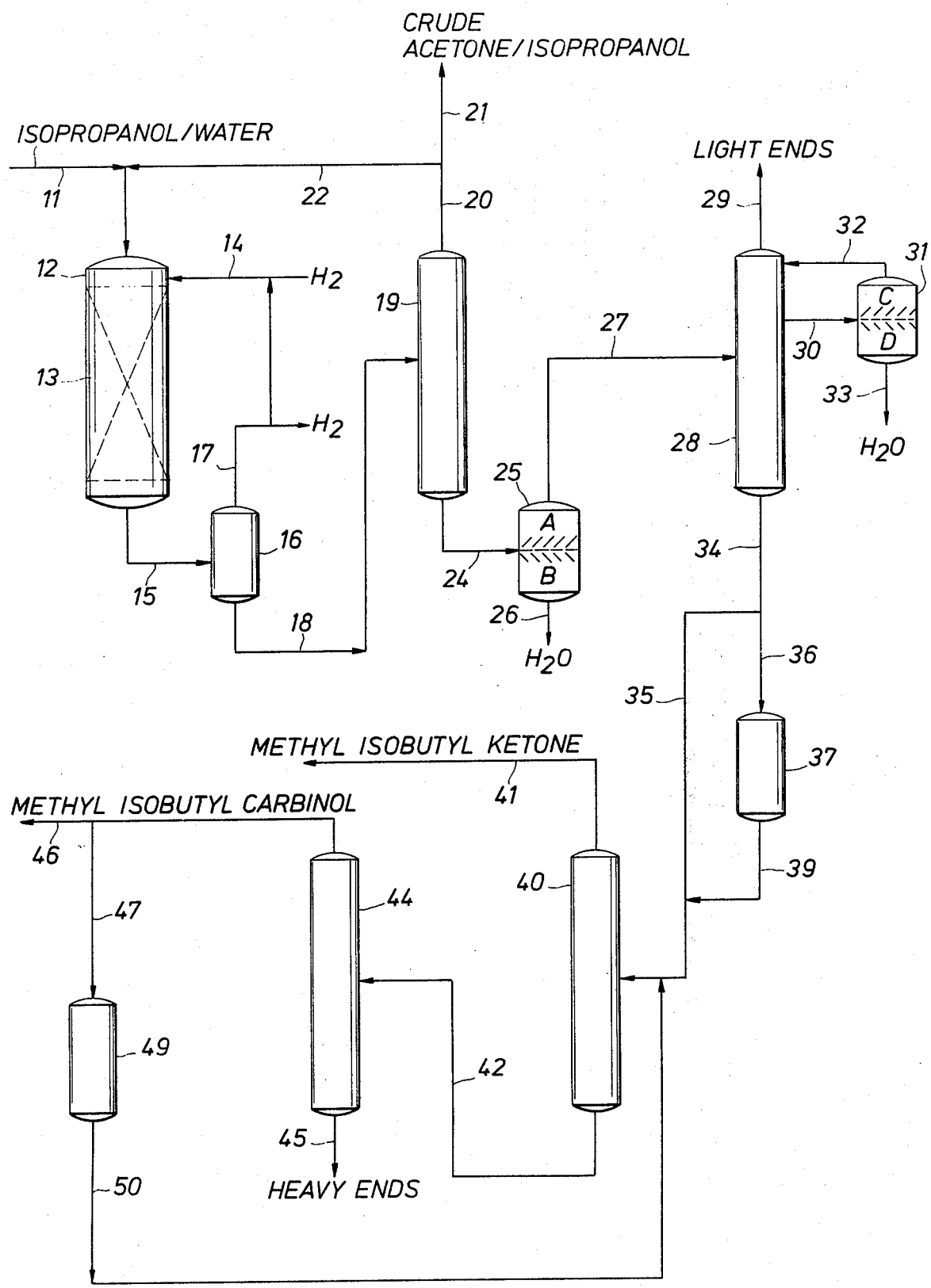

DEHYDROGENATION OF ALCOHOLS TO KETONES

This is a division of application Ser. No. 44,051, filed June 8, 1970, now U.S. Pat. No. 3,875,239, issued Apr. 1, 1975.

Background of the Invention

1. Field of the Invention.

This invention relates to processes and catalysts for the dehydrogenation of alcohols to ketones, and/or for the condensation of lower ketones to higher ketones. More specifically, it relates to a method for controlling, maximizing or minimizing the formation of ketone condensation products when secondary alcohols are catalytically dehydrogenated to ketones.

2. The Prior Art.

Certain lower ketones, for example dimethyl ketone (acetone) and methyl ethyl ketone are prepared on commercial scale by dehydrogenating secondary alcohols, for example isopropanol and sec-butanol, with zinc, copper and brass catalysts. Conventionally, these lower ketones can be converted into higher ketones, for example acetone can be converted into methyl isobutyl ketone, by a three-step process; first, the ketone (acetone) is condensed in the presence of caustic to form a diketone alcohol (diacetone alcohol), then the diketone alcohol is dehydrated to an unsaturated oxide (mesityl oxide) with a suitable dehydrogenation catalyst, and finally the unsaturated oxide is hydrogenated to higher ketone (methyl isobutyl ketone).

These three reactions, condensation, dehydration, and hydrogenation often occur to very minor extents during the initial alcohol dehydrogenation reaction. The amounts of higher ketone, for example, the methyl isobutyl ketone formed during acetone production, are often large enough to be deleterious to the lower ketone product quality but are seldom large enough to be economically recoverable. It is clearly desirable to have a method to control the formation of higher ketones, either to minimize their formation and thus reduce lower ketone product contamination or more importantly to increase their production to a point where they can be economically recovered and thus avoid complicated three-step conventional higher ketone production methods.

STATEMENT OF THE INVENTION

It has now been found that platinum or rhodium on a porous alumina support are effective catalysts for the dehydrogenation of lower alcohols to ketones, and/or for the condensation of lower ketones to higher ketones, and that by varying the average pore diameter of the porous alumina support the amount of ketone condensation products formed can be maximized or minimized. In general terms, as the average pore diameter of a porous platinum or rhodium on alumina catalyst is raised, the specificity of the dehydrogenation to the corresponding ketone is increased, and as the pore diameter is lowered, the proportion of higher ketones is increased. Thus, for example, when isopropanol is dehydrogenated with a small pore diameter alumina-supported catalyst, methyl isobutyl ketone is co-produced with acetone in economically recoverable high yields. When a large pore diameter alumina-supported platinum or rhodium catalyst is employed, high selectivity to acetone is achieved.

The invention will be described with reference to the accompanying drawing, wherein the sole FIGURE illustrates diagramatically an elevational view of one form of apparatus suitable for carrying out the process of the invention.

DETAILED DESCRIPTION OF THE INVENTION

Catalyst

Platinum or rhodium on alumina catalysts are employed in this invention. The platinum or rhodium content of the catalysts is suitably selected in the range of from 0.01% by weight platinum or rhodium (calculated as the respective metal based on the entire weight of catalyst) to about 1.0% by weight, with platinum or rhodium contents of 0.02% by weight to 0.75% by weight being preferred and platinum or rhodium contents of from 0.04% by weight to 0.50% by weight being most preferred. Higher and lower amounts of platinum or rhodium may be employed but higher amounts are unsuitably expensive and lower amounts give lower catalyst activity.

The platinum or rhodium is applied to the catalyst by conventional methods. One very suitable method is by impregnating a suitable aluminous support with a solution, preferably an aqueous solution, of a platinum compound, for example chloroplatinic acid ($H_2PtCl_6$) or tetrammine platinum hydroxide ($Pt(NH_3)_4(OH)_2$), or of a rhodium compound, for example rhodium nitrate ($Rh(NO_3)_3$). If desired, the support can simultaneously or separately be impregnated with solutions of other metals. Thus, impregnation with a titanium compound gives very favorable results in combination with platinum or rhodium. Impregnation with titanium isopropoxide ($Ti(OC_3H_7)_4$) from an anhydrous solution has proved very useful. After impregnation, the solvent can be removed by evaporation. When the platinum or rhodium is applied to the support as a compound, it is desirable to convert the said metal of the compound in question to a metallic state, as by reduction with hydrogen at a temperature above 150°C, and preferably above 250°C.

It should be noted that in the preparation of the catalyst one or more basic components may be added to the support, e.g., after the platinum or rhodium has been applied. It is more advantageous, however, to carry out the impregnation of the carrier in one single operation by applying the basic and noble metal components simultaneously.

The nature of the catalyst support employed is important. Suitable supports include the porous, non-acidic aluminas. The acidity of a catalyst support can be determined by the following procedure. A sample of catalyst support is contacted with isopropanol/water azeotrope vapor (87% IPA, 13% water) at a space velocity of 4 liters of liquid isopropanol azeotrope per liter of support per hour at a temperature of 370°C and a pressure of 6 atmospheres. After 20 hours, a sample is taken from the gas stream which had just passed over the support and the hydrocarbon content of the sample of the gas stream is determined. A support is regarded as non-acidic if less than 10% by weight of the total isopropanol component of the sample has been dehydrated to olefin. Catalyst supports which dehydrate less than 5% by weight of the isopropanol are preferred with supports which dehydrate less than 2% of the isopropanol being most preferred.

The average pore diameter of the porous alumina catalyst support is critical. The average pore diameter can be calculated using the formula:

$$\text{average pore diameter } (A) = 4 \times \frac{\text{pore volume (ml/g)}}{\text{specific surface area (m}^2\text{/g)}} \times 10^4$$

The specific surface area can be determined according to the BET method as explained by Paul H. Emmett in the second chapter of the book "Catalysis", Volume I (Reinhold Publishing Corporation, New York, 1954). The pore volume can be determined as described by A. Wheeler in the second chapter of Volume II of the book "Catalysis" (Reinhold Publishing Corporation, New York, 1955) by means of the BET method for pores of not too large diameters (up to about 100 A), and for larger pores by means of the mercury-porosimeter method likewise described in that latter chapter.

It has been found that a large specific surface area gives rise to the formation of a greater amount of oxygen-containing compounds having more carbon atoms per molecule than the starting alcohol which are referred to as condensation products) than a small specific surface area. If, in general, the formation of condensation products is to be kept low, it is recommended to use alumina carriers with a specific surface area of 5–100 m²/g, in particular of 10–80 m²/g. If, on the contrary, it is desired to produce a larger percentage of condensation products, such as methyl isobutyl ketone, the specific surface area should preferably exceed 100 m²/g, surface areas of up to 150 m²/g having proved to be particularly favorable.

The type of ketone product mixture produced is dependent on the average pore diameter of catalyst support. Catalyst supports having an average pore diameter not greater than 250 A, preferably less than 200 A, and of at least 150 A, are employed when maximum proportions of ketone condensation products, especially those ketones having twice as many carbons as the starting alcohols, are desired. Supports having an average pore diameter of greater than 250 A, preferably greater than 300 A and most suitably greater than 450 A are employed when it is desired to maximize the production of ketones of the same number of carbons as the starting alcohols. Many commercial aluminas generally have relatively small (less than 150 A) average pore diameters. The average pore diameter of such supports can be increased, if desired, by heating the support at a temperature above 900°C (preferably from 1000° to 1200°C) if desired in the presence of a fluxing agent such as boric acid. The duration of this treatment depends upon the temperature. For instance, a commercially available gamma-alumina with a specific surface area of 311 m²/g and an average pore diameter of 57 A on being heated at 1100°C for 6 hours is converted to an alumina with a specific surface area of 22.5 m²/g and an average pore diameter of 780 A.

Before or after the heating described, one or more of the basic catalyst components may be added to the carrier, for instance by impregnation with a solution thereof and evaporation of the solvent.

Alcohol and/or ketone Feedstock.

Acyclic, aliphatic mono-alcohols, i.e., alkanols containing from 3 to 6 carbon atoms, and/or lower ketones, are suitable feedstocks in the process according to the invention. Particularly suitable are the secondary aliphatic mono-alcohols with the secondary alkanols, isopropanol and sec-butanol being most preferred, and/or the corresponding ketones, particularly acetone and methyl ethyl ketone. The process according to the invention is particularly suitable for application to mixtures of alcohol and water, especially those mixtures of isopropanol and water, such as the azeotropic mixture of water and isopropanol (13% by weight water/87% by weight isopropanol) which is produced commercially. A somewhat more specialized feedstock which may be suitably used with the platinum or rhodium on alumina catalysts of the invention is the ketone-containing effluent of conventional zinc, copper or brass-catalyzed alcohol dehydrogenation, for example, the acetone, isopropanol/water mixture which results when isopropanol/water azeotrope is dehydrogenated with a brass catalyst. Such an effluent typically contains about 50 to 55% by weight acetone, 20 to 25% by weight isopropanol, 13 to 25% by weight water, and hydrogen. When such a ketone-containing feedstock is employed, very complete dehydrogenation of the isopropanol initially fed is achieved and either high selectivity to acetone is realized or an efficient co-production of acetone and methyl isobutyl ketone is achieved. Mixtures of alcohols and/or ketones, of course, can be used as starting materials.

Reaction Conditions.

The temperature at which the dehydrogenation reaction can be performed may vary within wide limits. Temperatures between 250° and 500°C are generally preferred. The amount of condensation products increases as the temperature is raised and the amount of ketone formed having the same number as carbon atoms as the starting alcohol decreases accordingly. Therefore, when ketone monomers are being prepared, temperatures in the range of from 250° to about 400°C are preferred and when condensation products are being maximized, temperatures in the range of from 350° to 500°C are preferred.

The pressure employed during the reaction according to the invention may vary within wide limits. In general, atmospheric pressures to pressures of 25 atmospheres are very suitable. At these pressures, the alcohol feedstock will be present as vapor. Pressures between 1 atmosphere and 10 atmospheres are preferred. At lower pressures, such as from atmospheric to 6 atmospheres, the selectivity to ketone monomers are somewhat greater than at higher pressures such as from 5 atmospheres to 10 atmospheres.

Catalyst activity is sustained if added hydrogen is present during the contact of the alcohol to be dehydrogenated with the catalyst. When the starting material, or one of the starting materials, is a ketone, the presence of hydrogen is, of course, essential.

Although the reaction may be performed batchwise, preference is given to a continuous process, i.e., a vapor stream containing the reaction components is passed, at a certain rate, over or through the catalyst. It is one of the advantages of the process according to the invention that high space velocities, expressed in liters of liquid alcohol or alcohol-containing liquid per liter of catalyst per hour (LHSV) may be applied without the conversion of alcohol decreasing unsuitably. LHSV's of up to about 25 liters/liter/hour and even higher are very suitable.

Ketone Products.

The ketones prepared by this invention have a wide range of application as solvents, plasticizers, blending agents, wax substitutes, detergents, and numerous other uses. Typical solvent applications include: acetone as a solvent for nitrocellulose, methyl isobutyl ketone as a solvent for cellulose esters, and methyl ethyl ketone as a solvent for lacquer resins.

A description of an exemplary process for the production of methyl isobutyl ketone from isopropanol using a small pore diameter alumina supported platinum or rhodium catalyst is provided by the accompanying drawing. Referring to the FIGURE, isopropanol/water azeotrope (87% isopropanol) is introduced as a vapor via line 11 into reactor 12 wherein it contacts a fixed catalyst bed 13. The non-acidic catalyst contains 0.25% by weight of platinum or rhodium on an alumina support having an average pore diameter of 150 A and additionally contains 0.5% by weight of sodium. Hydrogen is added to the reactor via line 14. A reaction product containing hydrogen, water, acetone, isopropanol, methyl isobutyl ketone, methyl isobutyl carbinol, and minor amounts of light ends and heavy ends is removed via line 15 to condenser 16 where all products, except hydrogen, are condensed. Hydrogen is removed via line 17 and optionally recycled to line 14. Other products are transferred via line 18 to fractionator 19, where acetone and unreacted isopropanol and some water are taken off as overhead through line 20 and either passed via line 21 to further fractionators not shown to recover purified acetone, or are recycled via line 22 to dehydrogenation reactor 14. A bottoms product is removed from fractionator 19 via line 24 to separator 25 where a water phase B is separated and removed via line 26. An organic phase A is separated and transferred via line 27 to fractionator 28, where light ends are overheaded and removed via line 29. A methyl isobutyl ketone/water azeotrope sidedraw is taken through line 30, condensed, and passed to separator 31 where a methyl isobutyl ketone phase C is separated and return as reflux via line 32 and a water phase D is separated and removed via line 33. Fractionator bottoms product is removed via line 34 and either passed directly to fractionator 40 via line 35 or optionally passed through lines 36 and 39 through hydrogenator 37, which hydrogenates any traces of mesityl oxide present. In fractionator 40, an overhead fraction of purified methyl isobutyl ketone is removed via line 41. A bottoms product of fractionator 40 is transferred to fractionator 44 via line 42 where heavy ends are separated as bottoms and removed via line 45 and an overhead of methyl isobutyl carbinol is either removed via line 46 or optionally passed via line 47 to dehydrogenator 49 where the methyl isobutyl carbinol is converted into methyl isobutyl ketone and then recycled to line 35 via line 50.

The following examples are illustrative of the practice of the invention. It is to be understood that these examples are given only for illustration and are not to be construed as limiting the invention in any way.

EXAMPLE I

Three platinum on alumina catalysts (Catalysts A, B and C) were prepared. The following aluminas were used as carriers for the preparation of catalysts:

For catalyst A an alumina with a specific surface area of 311 m$^2$/g, a pore volume of 0.44 ml/g, an average pore diameter of 57 A (calculated from these figures), and a sodium content of 0.05%w.

For catalyst B an alumina with a specific surface area of 312 m$^2$/g, a pore volume of 0.35 ml/g, an average pore diameter of 45 A (calculated from these figures) and a sodium content of 0.5%w.

The carrier for catalyst C was obtained by heating the alumina described for catalyst A for 6 hours at 1100°C. It had a specific surface area of 30.4 m$^2$/g and an average pore diameter of 580 A.

The non-acidic character of the carriers was demonstrated by means of an appropriate experiment as has been described in the text.

Catalysts containing 0.25%w of platinum were prepared by impregnating the three aluminas with a calculated amount of an aqueous solution of chloroplatinic acid, followed by drying at 120°C for 6 hours. The chloroplatinic acid was then converted into platinum by heating the catalyst in an atmosphere of hydrogen.

The three catalysts were tested for alcohol dehydrogenation performance. The alcohol-containing feed consisted of a mixture of 87%w isopropanol and 13%w of water. The pressure during the reaction was 3 atmospheres and the feed was passed over the catalyst at a space velocity of 4 liters of liquid per liter of catalyst per hour. The temperature during the reaction was about 270°C. After reaction for 6 hours the composition of the reaction product was determined. Table A shows that with catalyst C a high conversion of the isopropanol is attained with a high selectivity to acetone, while with catalysts A and B, a large amount of higher ketones is formed.

Table A

| | Catalyst | | | Reaction Products % Selectivity towards | | | |
|---|---|---|---|---|---|---|---|
| Type | Specific surface area of carrier m$^2$/g | Average pore diameter of carrier, A | Conversion of Isopropanol, % | Acetone | Methyl-isobutyl ketone + -carbinol | Oxygen Compounds with 9 carbon atoms | Hydrocarbons |
| A | 311 | 57 | 70 | 50 | 26 | 21 | 3 |
| B | 312 | 45 | 70 | 55 | 30 | 15 | 0.5 |
| C | 30.4 | 580 | 80 | 97 | 2 | <1 | <0.4 |

EXAMPLE II

An alumina as described as carrier for catalyst B in Example I was heated at 1100°C for 6 hours. After this period the surface area was 13 m$^2$/g and the average pore diameter 1070 A, the amount of hydrocarbons found in the determination of the acidic or non-acidic character of the carrier was 0.1%. This carrier was impregnated with an aqueous solution of chloroplatinic acid and dried at 120°C for 2 hours. The catalyst contained 0.05% platinum. The catalyst was heated to about 370°C under a stream of hydrogen, and, subsequently, a mixture of 87%w isopropanol and 13%w water, together with hydrogen (5 liters of hydrogen (calculated at 0°C and 1 atm) per 100 grams of isopropanol/water mixture) was passed over the catalyst at a pressure of 6 atm. Table B shows the composition of the reaction product at various times.

passed over this catalyst at a space velocity of 23 liters of liquid per liter of catalyst per hour. Table D shows the results.

Table D

| Reaction, Hours | Temp. of feed, °C | Temp. at end of Cat. Bed °C | Conversion, of isopropanol in feed, % | % Selectivity towrds: | | |
|---|---|---|---|---|---|---|
| | | | | Acetone | Methyl isobutyl ketone | Hydrocarbons |
| 20 | 405 | 394 | 66 | 89 | 10 | 1 |
| 90 | 411 | 401 | 66 | 88 | 11 | 1 |
| 162 | 419 | 410 | 66 | 87 | 12 | 1 |

EXAMPLE V

An alumina with a specific surface acrea of 256 m²/g and a pore volume of 0.65 ml/g was heated in air at 1100°C for 6 hours. After this treatment the material thus obtained had a specific surface area of 85.9 m²/g and a pore volume of 0.33 ml/g. The average pore Table B

| Reaction, Hours | Temp. at end of Cat. bed, °C | Space velocity, l/l/h | Con- version,% | % Selectivity towards: | | | |
|---|---|---|---|---|---|---|---|
| | | | | Acetone | Methyl isobutyl ketone | Methyl isobutyl carbinol | Oxygen compound with 9 C atoms |
| 27 | 354 | 4 | 93.8 | 89.9 | 9.5 | 0.5 | — |
| 46 | 358 | 4 | 94.1 | 89.4 | 9.6 | 0.9 | — |
| 77 | 358 | 4 | 92.1 | 89.4 | 9.8 | 0.7 | — |
| 167 | 358 | 4 | 92.3 | 89.9 | 8.9 | 0.9 | — |
| 194 | 359 | 2 | 93.9 | 78.0 | 19.6 | 2.3 | 0.3 |
| 243 | 357 | 2 | 94.3 | 79.3 | 18.3 | 2.5 | 0.4 |
| 313 | 360 | 2 | 93.9 | 81.7 | 16.4 | 1.6 | 0.3 |

EXAMPLE III

A large pore catalyst was prepared as described in Example II. After heating to about 370°C under a stream of hydrogen, sec-butanol and hydrogen (5 liters of hydrogen calculated at 0°C and 1 atm per 100 grams of sec-butanol) were passed over the catalyst at a pressure of 6 atm and a space velocity of 4 liters of liquid per liter of catalyst per hour. Table C shows the results.

Table C

| Re- action, Hours | Temp. at end of cat. bed, °C | Conversion % | % Selectivity towards | |
|---|---|---|---|---|
| | | | Methyl ethyl ketone | oxygen compounds with 8 carbon atoms |
| 51 | 358 | 93.3 | 96.2 | 3.5 |
| 73 | 358 | 92.5 | 96.3 | 3.5 | diameter, determined with the aid of a mercury porosimeter, was found to be 200 A.

This carrier material was subsequently charged with 0.25% of rhodium and 1.5%w of sodium by impregnation with the calculated amounts of an aqueous solution containing rhodium nitrate and sodium nitrate, in such a way that the pores were just filled, followed by drying at 120°C and heating in air at 500°C for 3 hours.

Over the catalyst thus obtained a feed was passed which consisted of 57.5%w of acetone, 25%w of isopropyl alcohol and 17.5%w of water, together with such a quantity of hydrogen that the $H_2$/acetone molar ratio was 1.0. During the reaction the pressure was maintained at 6 atm abs. In two experiments the space velocities (LHSV) amounted to 5 and 10 liters of feed per liter of catalyst per hour, respectively. The results are given in Table E.

Table E

| Space velocity (LHSV), $l.l^{-1}.h^{-1}$ | temp. at end of cat. bed, °C | conversion of isopropyl alcohol in feed, % | % selectivity towards: | | |
|---|---|---|---|---|---|
| | | | acetone | methylisobutyl ketone | hydrocarbons |
| 5 | 320 | 72 | 92 | 7 | 1 |
| 10 | 350 | 83 | 89 | 10 | 1 |

EXAMPLE IV

A catalyst as described in Example II was prepared with the difference that the amount of platinum was 0.25%w. A mixture of 52.9%w acetone, 24.0%w isopropanol and 23.1%w water and hydrogen, obtained by dehydrogenation of an isopropanol/water mixture (weight ratio 87/13) over a copper-zinc alloy, was

EXAMPLE VI

A carrier material as described in example V was charged with 2%w of titanium (as titanium tetraisopropoxide dissolved in n-hexane). After drying at 120°C the impregnated carrier was heated for 3 hours at 500°C. Subsequently, this material was charged with 0.25%w of platinum and 1.5%w of sodium by impregnation with the calculated amounts of an aqueous solution containing sodium hexachloroplatinate and sodium hydroxide in such a way that the pores were just filled, followed by drying at 120°C and heating in air at 500°C for 3 hours.

Over this catalyst a feed was passed which consisted of 94.8%w of acetone, 4.3%w of isopropylalcohol and 0.9% of water, together with such a quantity of hydrogen that the intake molar ratio H$_2$/acetone was 1.0. The working pressure of the reactor system was 6 atm abs. The space velocity (LHSV) was adjusted at 10 l feedstock (1 cat. h)$^{-1}$. The reactor inlet temperature was 260°C, resulting in an oulet temperature of 300°C. The liquid reaction product excluding water consisted of 60%w of acetone, 8%w of isopropyl alcohol, 23%w of methyl isobutyl ketone, 1.8%w of mesityl oxide and methyl isobutyl carbinol, and 7.2% of C$_9$ oxygen containing compounds.

EXAMPLE VII

The catalyst described in example VI was contacted with a feedstock having the composition: 61.3%w of acetone, 23.85%w of isopropyl alcohol, 0.2%w of methyl isobutyl ketone and 14.7%w of water, together with such a quantity of hydrogen that the intake molar ratio H$_2$/acetone was 1.0. The working pressure of the reactor system was again 6 atm abs. The feed rate was 10 liters liquid feed per liter of catalyst per hour (LHSV). The reactor inlet temperature was 354°C, the reactor outlet temperature 380°C. The composition of the liquid reaction product (excluding water) was 68%w of acetone, 4.0%w of isopropyl alcohol, 21.0%w of methyl isobutyl ketone, 1.3%w of mesityl oxide and methyl isobutyl carbinol, and 5.7%w of C$_9$ oxygen containing compounds.

EXAMPLE VIII

A carrier prepared as described in Example V was charged with 0.25% of platinum and 1.5% of sodium by impregnation with the calculated amounts of an aqueous solution sodium hexachloroplatinate and sodium hydroxide in such a way that the pores were just filled, followed by drying at 120°C and calcining in air for 3 hours at 500°C. Over this catalyst the same feed as in example VII was passed at the same LHSV of 10, together with the same amount of hydrogen (molar ratio H$_2$/acetone = 1.0). Also the pressure was the same. The reactor inlet temperature was 365°C. The reactor outlet temperature 380°C.

The composition of the liquid reaction product (excluding water) was as follows in %w.

| | |
|---|---|
| Acetone | 80.4 |
| Isopropyl alcohol | 7.1 |
| Methyl isobutyl ketone | 10.5 |
| Mesityl oxide and Methyl isobutyl carbinol | 0.9 |
| C$_9$ oxy compounds | 1.1 |

We claim as our invention:
1. A process for converting an acyclic aliphatic secondary monoalcohol having from 3 to 6 carbon atoms into an aliphatic ketone having the same number of carbon atoms as the secondary monoalcohol which comprises passing the monoalcohol over a catalyst consisting essentially of from 0.01% by weight to 1% by weight of platinum on a non-acidic porous alumina support having an average pore diameter of greater than 250A and a specific surface area from about 5 to 100 m$^2$/g at a temperature of from 250° to 400°C and a pressure of from 1 atmosphere to 5 atmospheres.

2. The process in accordance with claim 1 wherein the monoalcohol is isopropanol or sec-butanol and the ketone produced is acetone or methyl ethyl ketone.

3. The process in accordance with claim 2 wherein the catalyst contains from 0.2% by weight to 0.75% by weight of platinum, and wherein the porous non-acidic alumina has an average pore diameter of greater than 300 A.

* * * * *